(12) United States Patent
McShane et al.

(10) Patent No.: US 8,617,225 B2
(45) Date of Patent: Dec. 31, 2013

(54) SPLINE DRIVE FOR THREADED POST-TYPE BONE ANCHORS

(75) Inventors: Edward McShane, Collegeville, PA (US); Josef Gabelberger, West Chester, PA (US); Joseph Capozzoli, Mount Laurel, NJ (US)

(73) Assignee: DePuy Synthes Products, LLC, Raynham, MA (US)

( * ) Notice: Subject to any disclaimer, the term of this patent is extended or adjusted under 35 U.S.C. 154(b) by 413 days.

(21) Appl. No.: 12/645,797

(22) Filed: Dec. 23, 2009

(65) Prior Publication Data

US 2010/0217333 A1 Aug. 26, 2010

Related U.S. Application Data

(60) Provisional application No. 61/140,716, filed on Dec. 24, 2008.

(51) Int. Cl.
- *A61B 17/04* (2006.01)
- *A61B 17/86* (2006.01)
- *A61F 2/08* (2006.01)

(52) U.S. Cl.
USPC ............... 606/305; 606/308; 411/402

(58) Field of Classification Search
USPC .......... 606/305, 307, 308, 325, 104; 411/402, 411/403, 405, 406
See application file for complete search history.

(56) References Cited

U.S. PATENT DOCUMENTS

| | | | |
|---|---|---|---|
| 364,587 A | 6/1887 | Higgin | |
| 662,134 A | 11/1900 | Rodd | |
| 1,075,710 A | 10/1913 | Goodwin | |
| 1,861,640 A | 6/1932 | McCabe | |
| 2,397,216 A | 3/1946 | Stellin | |
| 2,800,829 A | 7/1957 | West | |
| 3,295,572 A | 1/1967 | Wing | |
| 3,354,757 A * | 11/1967 | Grimm et al. | ........... 81/176.1 |
| 3,969,974 A | 7/1976 | Lejdegard | |
| 4,006,660 A | 2/1977 | Yamamoto et al. | |
| 4,010,670 A | 3/1977 | Lejdegard | |
| 4,073,160 A | 2/1978 | Perret | |
| 4,228,723 A | 10/1980 | Cunningham | |
| 4,361,412 A | 11/1982 | Stolarczyk | |
| 4,459,074 A | 7/1984 | Capuano | |

(Continued)

FOREIGN PATENT DOCUMENTS

| | | |
|---|---|---|
| DE | 20 2006 009843 | 9/2006 |
| FR | 1427828 | 2/1966 |

(Continued)

OTHER PUBLICATIONS

International Patent Application No. PCT/US2009/069391: International Search Report and Written Opinion dated Jul. 5, 2010, 12 Pages.

*Primary Examiner* — Andrew Yang
(74) *Attorney, Agent, or Firm* — Woodcock Washburn LLP

(57) ABSTRACT

A threaded bone anchor includes a plurality of recesses formed lengthwise along an exterior cylindrical surface for engagement with a driver instrument through which a user applies clockwise or counterclockwise torque for the insertion or removal of the bone anchor into and from bone. The bone anchor includes a cross-sectional geometry that minimizes the anchor's outer diameter, survives high insertion/removal torque without compromising the anchor's bending/shear strength, and allows a mating clamp to be attached to the entire non-threaded surface, including the recessed portion.

37 Claims, 10 Drawing Sheets

(56) References Cited

U.S. PATENT DOCUMENTS

| | | | |
|---|---|---|---|
| 4,979,858 A | 12/1990 | Van Allman et al. | |
| 5,019,080 A | 5/1991 | Hemer | |
| 5,279,190 A | 1/1994 | Goss et al. | |
| 5,435,680 A | 7/1995 | Schuster | |
| 5,641,258 A | 6/1997 | Sala | |
| 6,077,267 A * | 6/2000 | Huene | 606/916 |
| 6,149,653 A | 11/2000 | Deslauriers | |
| 6,341,546 B1 | 1/2002 | Totsu | |
| 6,357,981 B1 | 3/2002 | Lanham et al. | |
| 6,398,785 B2 | 6/2002 | Carchidi et al. | |
| 6,402,749 B1 | 6/2002 | Ashman | |
| RE37,868 E | 10/2002 | Hillis et al. | |
| 6,716,214 B1 | 4/2004 | Jackson | |
| 6,997,085 B2 | 2/2006 | Yamamoto | |
| 7,174,811 B2 | 2/2007 | Wright | |
| 7,316,535 B2 | 1/2008 | Chen | |
| 7,727,235 B2 * | 6/2010 | Contiliano et al. | 606/86 A |
| 2001/0004694 A1 | 6/2001 | Carchidi | |
| 2002/0173822 A1 * | 11/2002 | Justin et al. | 606/232 |
| 2005/0251137 A1 | 11/2005 | Ball | |
| 2006/0293677 A1 | 12/2006 | Oepen | |

FOREIGN PATENT DOCUMENTS

| | | | |
|---|---|---|---|
| WO | WO 2004/043278 A1 | 5/2004 | |
| WO | WO 2005/122926 A1 | 12/2005 | |
| WO | WO 2010/075505 | 7/2010 | |

* cited by examiner

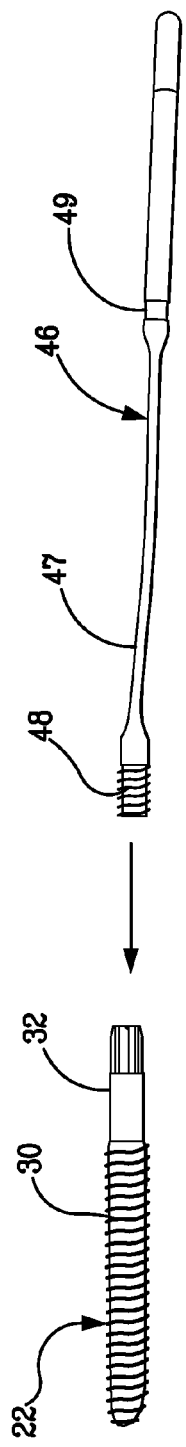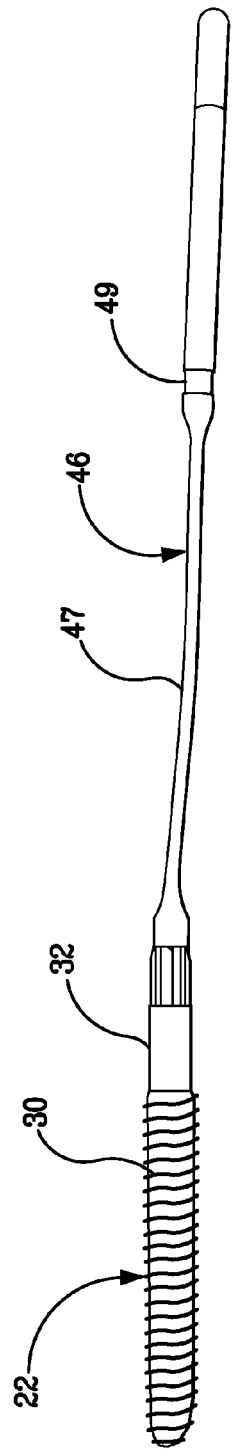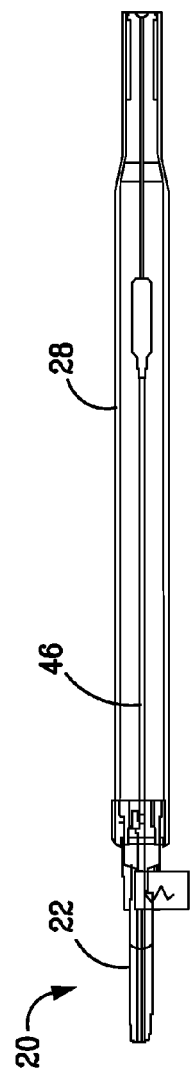
FIG. 5A
FIG. 5B
FIG. 5C

US 8,617,225 B2

SPLINE DRIVE FOR THREADED POST-TYPE BONE ANCHORS

CROSS REFERENCE TO RELATED APPLICATIONS

This Application claims priority to U.S. Provisional Patent Application No. 61/140,716, filed Dec. 24, 2008, the disclosure of which is hereby incorporated by reference as if set forth in its entirety herein.

TECHNICAL FIELD

The present invention relates generally to orthopedics, and in particular relates to a bone anchor incorporating a spline drive mechanism.

BACKGROUND

A variety of fixation devices for the reduction of bone or bone fragments or for spinal fixation are well known. Spinal fixation devices including intervertebral implants, spinal rods, and the like, are used to replace intervertebral discs, fuse or align adjacent vertebrae, and address other spinal issues. Long bone fixation devices commonly include both external and internal fixators that are attached to underlying bone. Spinal fixation devices and long bone fixation devices typically are affixed to underlying bone via one or more bone anchors.

For instance, a typical bone plate includes screw holes that accommodate bone screws which are drilled into underlying bone on opposing sides of a fracture to join bone segments together. A typical cervical spine implant can likewise include screw holes that accommodate screws which are drilled into adjacent vertebral bodies in order to fix the position of the implant. In certain applications it is desired to provide relatively small bone screws. For instance, spinal screws are having thread and head diameters less than 10 mm are commonly used. Bone screws of this size can become compromised when exposed to high torque/force that are applied when drilling, tapping, or otherwise inserting the anchor into underlying bone.

What is desirable is bone anchor configured to accept high torque/force without compromising the anchor's bending/shear strength.

SUMMARY

A bone anchor is provided, including an externally threaded shaft extending along a longitudinal axis, and a head connected to the shaft. The head defines a spline drive mechanism including plurality of equidistantly spaced longitudinally elongate recesses extending into the head such that each recess defines a pair of spaced side walls each defining opposing ends.

BRIEF DESCRIPTION OF THE DRAWINGS

The foregoing summary, as well as the following detailed description of a preferred embodiment of the application, will be better understood when read in conjunction with the appended drawings. For the purposes of illustrating the bone anchor of the present application, there is shown in the drawings a preferred embodiment. It should be understood, however, that the application is not limited to the precise arrangements and instrumentalities shown. In the drawings:

FIG. 5A is a side elevation assembly view of the bone anchor assembly including an auxiliary extension configured to be attached to the bone anchor;

FIG. 5B is a side elevation view of the bone anchor assembly illustrated in FIG. 5A, wherein the auxiliary extension is attached to the bone anchor;

FIG. 5C is a sectional side elevation view of the bone anchor assembly illustrated in FIG. 5B, showing the driver instrument attached to the bone anchor;

DETAILED DESCRIPTION

Figure 1A:
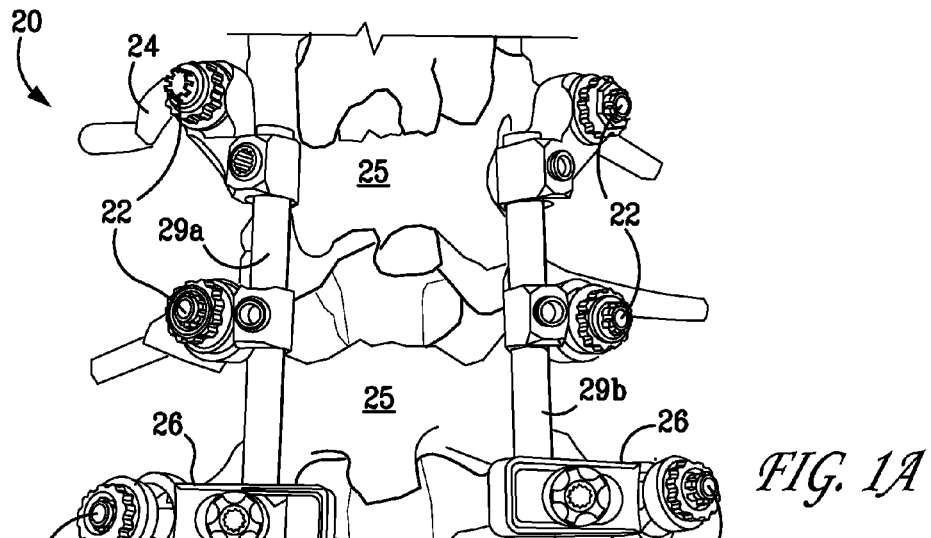
FIG. 1A is a perspective view of a spine fixation assembly including a plurality of bone anchors attached to pedicles of adjacent vertebrae, clamps attached to the bone anchors, and fixation rods connected between the clamps.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the bone anchor and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Referring to FIG. 1A, bone fixation assembly 20 includes a plurality of bone anchors 22 attached to underlying bone and joined by a fixation member, illustrated as an internal spinal fixation rod 29. In accordance with alternative embodiments, the fixation member can alternatively be an internal bone fixation plate, an external spinal fixation rod, or any internal or external fixation member configured to stabilize any bones via threaded anchors. In accordance with the illustrated embodiment, the bone fixation assembly 20 is illustrated as a spine fixation assembly whereby the anchors are attached to the pedicles 24 of a plurality of vertebrae 25 to be fixed. Thus, the bone anchors 22 can be provided as vertebral anchors, though the anchors can alternatively be configured for attachment to any underlying bone or bone segment as desired. In the illustrated bone fixation assembly 20, a clamp connector 26 is attached to each bone anchor 22 at one end. The clamp connector 26 extends inwardly to another end that is attached to the fixation rod 29. Accordingly, a first fixation rod 29a and a second fixation rod 29b extend generally along the caudal-cranial direction to fix the vertebrae as desired. In accordance with one embodiment, the bone fixation can be provided as a USS Fracture Assembly, commercially available from Synthes, Inc, having a place of business in West Chester, Pa. Unless otherwise indicated, the bone fixation system 20 and its components can be manufactured from any suitable biocompatible material known in the art including but not limited to 316L stainless steel, cobalt-chrome, CP titanium, Ti alloys including, but not limited to Ti-7A1-6Nb, TAV, or Ti-Moly, polymers such as PEEK, or allograft bone. The bone anchor 22 can further be coated with a bone-growth stimulating surface such as hydroxyapatite, plasma-sprayed titanium, anodic plasma spray coating, etc.

Figure 1B:
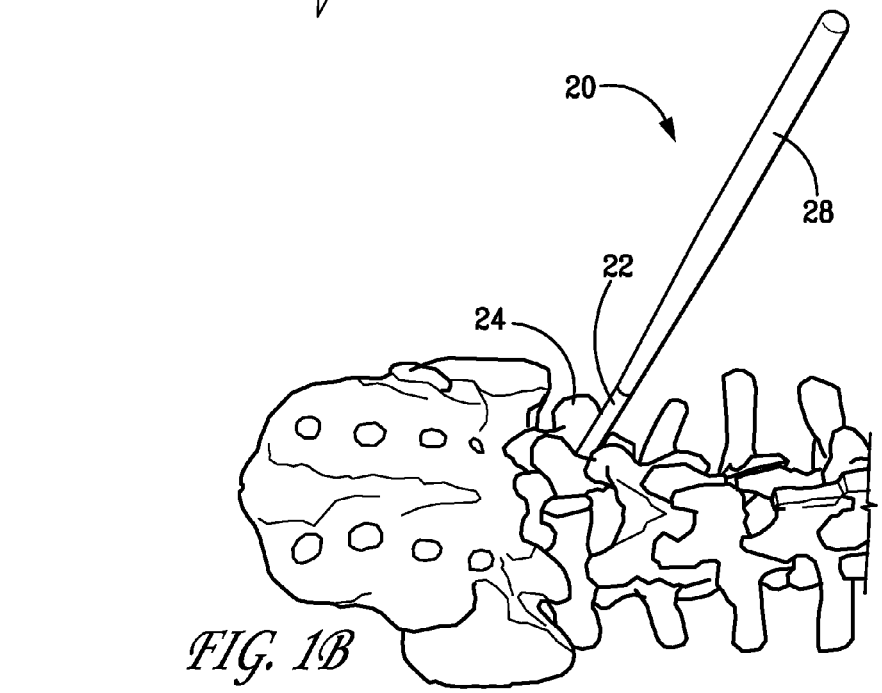
FIG. 1B is a perspective view of a bone anchor assembly including driver instrument attached to one of the bone anchors FIG. 1A, and attaching the bone anchor to a pedicle.

As shown in FIG. 1B, the bone anchor assembly 20 can include the bone anchor 22 and a driver instrument 28 configured to be attached to the bone anchor 22 so as to impart a driving torque or force onto the bone anchor 22 that causes the bone anchor 22 to attach to the underlying bone, such as a vertebral body or pedicle, a long bone in the arm, (ex. Humerus), leg (ex. femur) or pelvis, and/or a smaller bones (in the hands, feet, head, face, and the like)

Referring now to FIGS. 2A-B and 4A-D, the bone anchor 22 includes a shaft 30 that extends longitudinally along a central longitudinal axis L1. The shaft 30 defines longitudinally opposing proximal, or upper, and distal, or lower, ends 30a and 30b, respectively, and a head 32 integrally coupled to the proximal end 30a. The distal end 30b of the shaft 30 is configured to be attached to underlying bone. In particular, helical threads 34 extend radially out from the shaft 30 at locations at and between the proximal and distal ends 30a-b that are configured to engage underlying bone. Thus, when the head 32 receive a driving torque/force from the driver instrument 28 (for instance when inserting the anchor into an underlying bone, or removing the anchor from underlying bone), the threads 34 advance into the underlying bone.

The threads 34 can be continuous as illustrated or discontinuous so as to define a plurality of teeth that define threads having multiple starts (for instance double lead, triple lead, and the like). Thus, a substantial entirety of the shaft 30 can be threaded, or only a potion of the shaft can be threaded as in a lag screw used in long bone fixation. As illustrated in FIG. 2B, the threads 34 define an outer diameter OD that can increases in a direction from the distal end 30b toward the proximal end 30a, or can remain substantially constant between the proximal and distal ends 30a-b. It should thus be appreciated that the bone anchor 22 can alternatively be provided as a locking screw within a bone anchor or rod connector assembly, as desired. The bone anchor 22 can additionally or alternatively be self-tapping if desired, and/or can be configured to attach within a predrilled bore formed in the underlying bone. The bone anchor 22 can be provided as a Schanz or post-type bone anchor, or any alternatively constructed bone anchor as desired.

The head 32 includes an annular body 36 that defines a radially outer surface 38. The head 32 can be cannulated if desired, so as to define a radially inner surface 40 opposite the radially outer surface 38. Of course, the head 32 can assume any other suitable alternative shape as desired. The head 32 defines a proximal, or upper, end 32a and a distal, or lower, end 32b, such that the proximal end 32a of the head defines a proximal end of the bone anchor, and the distal end 30b of the shaft defines a distal end of the bone anchor 22. The distal end 32b of the head 32 is integrally coupled to the proximal end 30a of the shaft 30, either directly or indirectly via an unthreaded neck 41, which can provide a stop of larger diameter than the head, but not necessarily larger than the diameter of the bone threads that is coupled between the proximal end 30a of the shaft 30 and the distal end 32b of the head 32. The proximal end 32a of the annular body 36 defines a longitudinally outer end 33 that defines an annular longitudinally outer lip 35.

The outer surface 38 of the annular body 36 can be cylindrical as illustrated, that extends along the central longitudinal axis L1 as illustrated. Thus, the shaft 30 and the head 32 can be longitudinally co-extensive, or extend along the same longitudinal axis. The outer surface 38 defines a diameter or other cross-sectional outer dimension that can be the same as, greater than, or less than, the outer diameter OD of the threads 34.

Figure 2A:
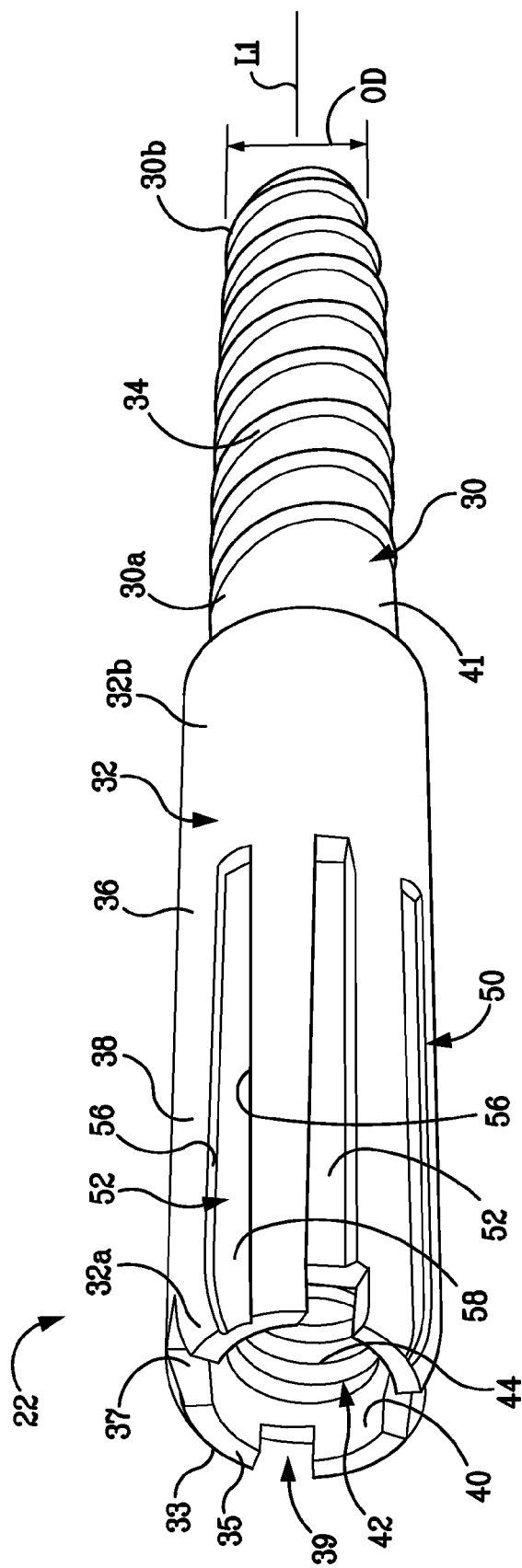
FIG. 2A is a perspective view of the bone anchor illustrated in FIG. 1B.
Figure 2B:
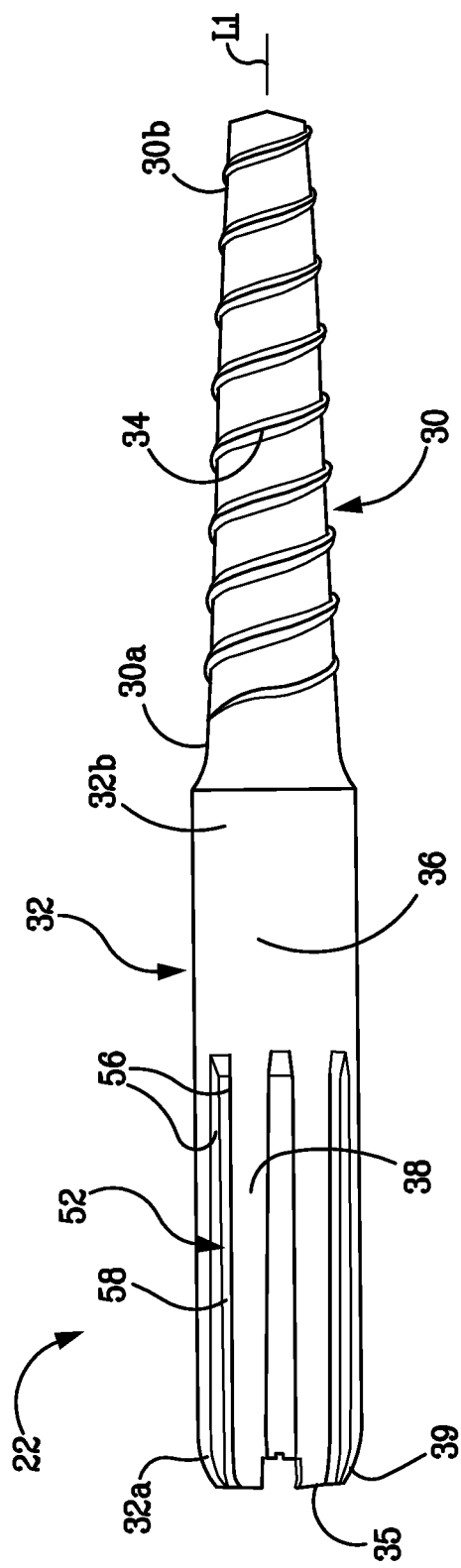
FIG. 2B is a side elevation view of the bone anchor of FIG. 2A.

With continuing reference to FIGS. 2A-B and with further reference to FIGS. 5A-B, the head 32 can define a bore 42 extending longitudinally distally through the longitudinally outer end 33 and radially surrounded by the annular lip 35 and the annular body 36. The bore 42 terminates within the annular body 36, and thus does not extend entirely through the bone anchor 22. The bore 42 defines the radially inner surface 40, which can present helical threads 44 projecting inwardly into the bore. Thus, the head 32 includes an engagement member configured to attach an auxiliary device, such as a locator 46. The locator 46 can include a longitudinally elongate body 47 that defines a cylindrical proximal end 46a having an engagement member in the form of helical threads 48 extending therefrom. The threads 48 and 44 are configured to mate so as to attach the locator 46 to the bone anchor 22.

Certain embodiments appreciate that the attachment of the bone anchor 22 to an underlying pedicle involves displacing a large amount of soft tissue in order to access the pedicle. Once the anchor 22 is attached to the pedicle, the soft tissue can return to its normal position. The elongate body 47 can be in the form of a flexible wire having a marker 49 at its distal end 46b positioned to extend beyond the soft tissue so that the anchor 22 can be easily identified, for instance when it is desired to attach clamps or other structure to the anchor 22. For example, the marker 49 can be colored differently than the surrounding structure of the body 47. The locator 46 can define any length as desired, such as between approximately 25 mm and approximately 200 mm. Once the bone fixation assembly 20 has been completed, the threads 48 of the locator 46 can be removed from the anchor head 32, thereby detaching the locator 46 from the bone anchor 22.

The head 32 can include an external spline drive mechanism 50 formed in the outer surface 38 of the head 32 that is configured to attach to a complementary engagement member of the driver instrument 28. Thus, the spline drive mechanism 50 can be referred to as an external spline drive mechanism. In particular, the head 32 defines a plurality of recesses 52 projecting into the radially outer surface 38 in a radially inward direction. The recesses 52 are longitudinally elongate, and thus parallel with the longitudinal axis L1. The recesses 52 are circumferentially spaced about the head 32 and configured to engage the driver instrument 28. In accordance with one embodiment, eight recesses 52 are circumferentially spaced equidistantly about the outer surface 38 of the head 32, though it should be appreciated that the head 32 can alternatively include any number of recesses 52 as desired, such as four, six, ten, twelve or more recesses 52.

Each recess 52 defines a pair of opposing radially extending side walls 56 and a base 58 disposed and connected between the radially inner ends of the side walls 56. It should be appreciated that the side walls 56 can extend radially, meaning that the side walls can extend in a pure radial direction or in a direction that includes a radial directional component. The side walls 56 of each recess 52 can extend along intersecting directions. For instance, the side walls 56 can converge toward each other with respect to a radially outward direction, or can diverge away from each other with respect to a radially outward direction. Alternatively still, the side walls 56 can extend parallel to each other. Additionally, portions of the side walls 56 of each recess 52 can be parallel, while other portions can converge or diverge. In accordance with the illustrated embodiment, the side walls 56 diverge away from each other with respect to a radially outward direction so as to provide an increased torque-receiving surface area, thereby increasing the torsional strength of each recess 52.

The base 58 can extend circumferentially, meaning that the base 58 can extend in a pure circumferential direction, or in a direction that includes a circumferential directional component, including a direction that extends tangential to the circumferential direction. The base 58 of each recess 52 can be perpendicular to one or both of the side walls 56, or can define an acute or obtuse angle with respect to one or both of the side walls 56. Within any or all of the recesses 52, the side walls 56 may be blended into the base 58 with radii, angled/chamfered corners, or filleted corners. The head 32 thus defines a first cross-sectional distance or diameter D1 defined by the radially outer surface 38 at opposing locations between adjacent recesses 52, and a second cross-sectional distance or diameter D2 defined by the outer surface 38 as defined by the base 58 of opposing recesses 52 that is less than the first distance or diameter D1 (see FIGS. 4C-D). The first distance D1 can be substantially equal to the outer diameter OD of the threads 34. The second distance or diameter D2 can increase along the tapered region 59 at the distal end of at least one, and up to all, of the recesses 52. In this regard, while the head 32 is illustrated as having a cylindrical outer surface 38, it is appreciated that the head 32 can define any alternative geometric shape as desired. For instance, the head 32 can define any desired polygon, such as an octagon corresponding to the eight recesses 52.

The bases 58 include a tapered region 59 that flares radially outwardly with respect to a longitudinal direction from the proximal end 32a of the head 32 toward the distal end 32b of the head 32. Accordingly, the distance or diameter between the radially inner surfaces of opposing bases 58 can increase at the distal end 32b of the head 32, for instance at the distal 2-5 mm of the recess 52, while the distance or diameter between the radially inner surfaces of opposing bases 58 at proximal end 32a of the head 32 is substantially constant. In accordance with one embodiment, the distance or diameter between the radially inner surfaces of opposing bases 58 along the proximal 5-10 mm can be substantially constant at approximately 4.2 mm.

Bone anchors of the type illustrated with respect to the bone anchor 22 are relatively small. In accordance with one embodiment, the outer diameter of the threads 34 and the outer diameter of the outer surface 38 are within the range of approximately 0.5 mm and approximately 9 mm, such as between approximately 0.5 mm and approximately 2 mm, between approximately 2 mm and approximately 4 mm, and between approximately 4 mm and approximately 9 mm. In accordance with one embodiment, the diameter of the inner surface 40 is within the range of approximately 1 mm and 8 mm, such as between approximately 1 mm and 6 mm, for instance between approximately 4 mm and approximately 6 mm at locations circumferentially between recesses 52. The annular body 36 can define a thickness extending normally between the outer surface 38 and the inner surface 40 of between approximately 0.25 mm and approximately 5 mm, such as between approximately 3 mm and approximately 5 mm. The head 32 can extend longitudinally a length within the range of approximately 5 mm and 50 mm, such as between approximately 17 mm and approximately 20 mm in accordance with the illustrated embodiment. Advantageously, the head 32 is constructed so as to receive and transmit levels of torque that allow the threads 34 to be driven into underlying dense bone, in spite of the small size of the bone anchor 22, and in particular of the head 32 and shaft 30. In accordance with one embodiment, the bone anchor 22 is configured to receive torque/force above at and above ten Newton-meters (10 Nm) without bending, yielding, fracturing or failing, for instance when the bone anchor 22 is driven into underlying dense bone between approximately 5 mm and approximately 100 mm in depth.

With continuing reference to FIG. 2A, the head 32 can define a plurality of notches 37 extending longitudinally into the annular lip 35. The notches 37 can define substantially rectangular or alternatively shaped cutouts or pockets 39 that are equidistantly spaced circumferentially about the lip 35. In accordance with one embodiment, each pocket 39 is longitudinally aligned with a corresponding one of the recesses 52. As illustrated, the head 32 includes four pockets 39 aligned with a corresponding four of the recesses 52, such that recesses aligned with pockets 39 are separated by recess that are not aligned with a corresponding pocket. It should be appreciated, of course, that the head 32 can alternatively include any number of pockets 39 as desired. In accordance with another embodiment, the lip 35 is devoid of pockets 39, and is thus circumferentially continuous at its longitudinally outer end.

Figure 3:
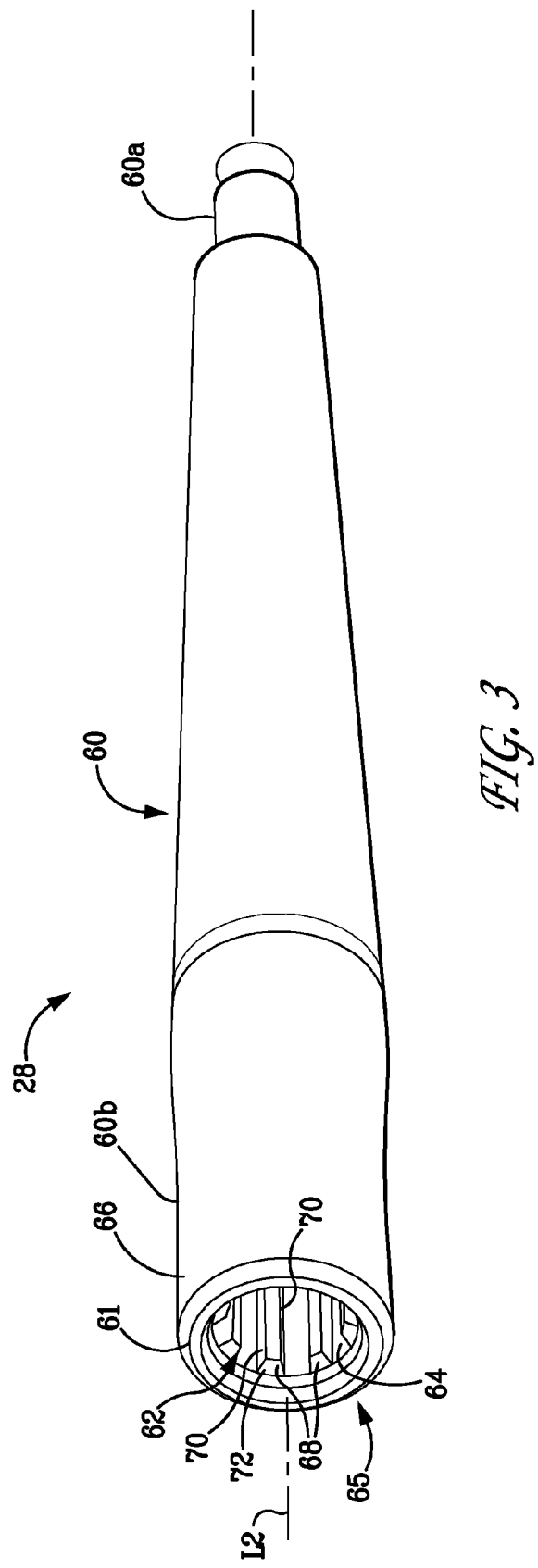
FIG. 3 is a perspective view of the driver instrument illustrated in FIG. 1B.
Figure 4A:
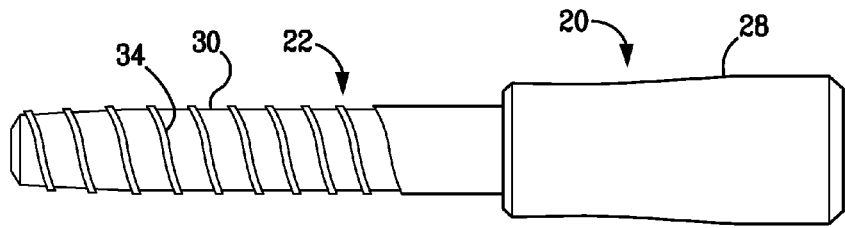
FIG. 4A is a partial side elevation view of the bone anchor assembly illustrated in FIG. 1B, showing the driver instrument attached to the bone anchor.
Figure 4B:
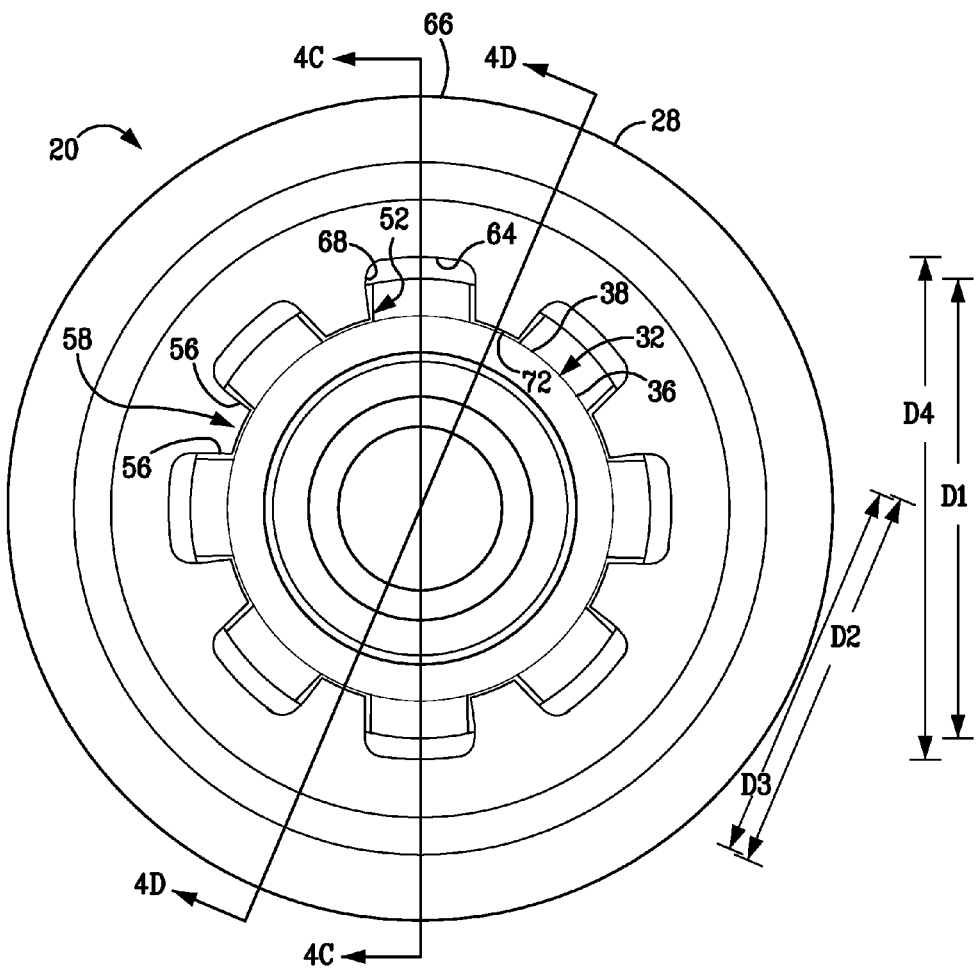
FIG. 4B is an end elevation view of the bone anchor assembly illustrated in FIG. 4A.
Figure 4C:
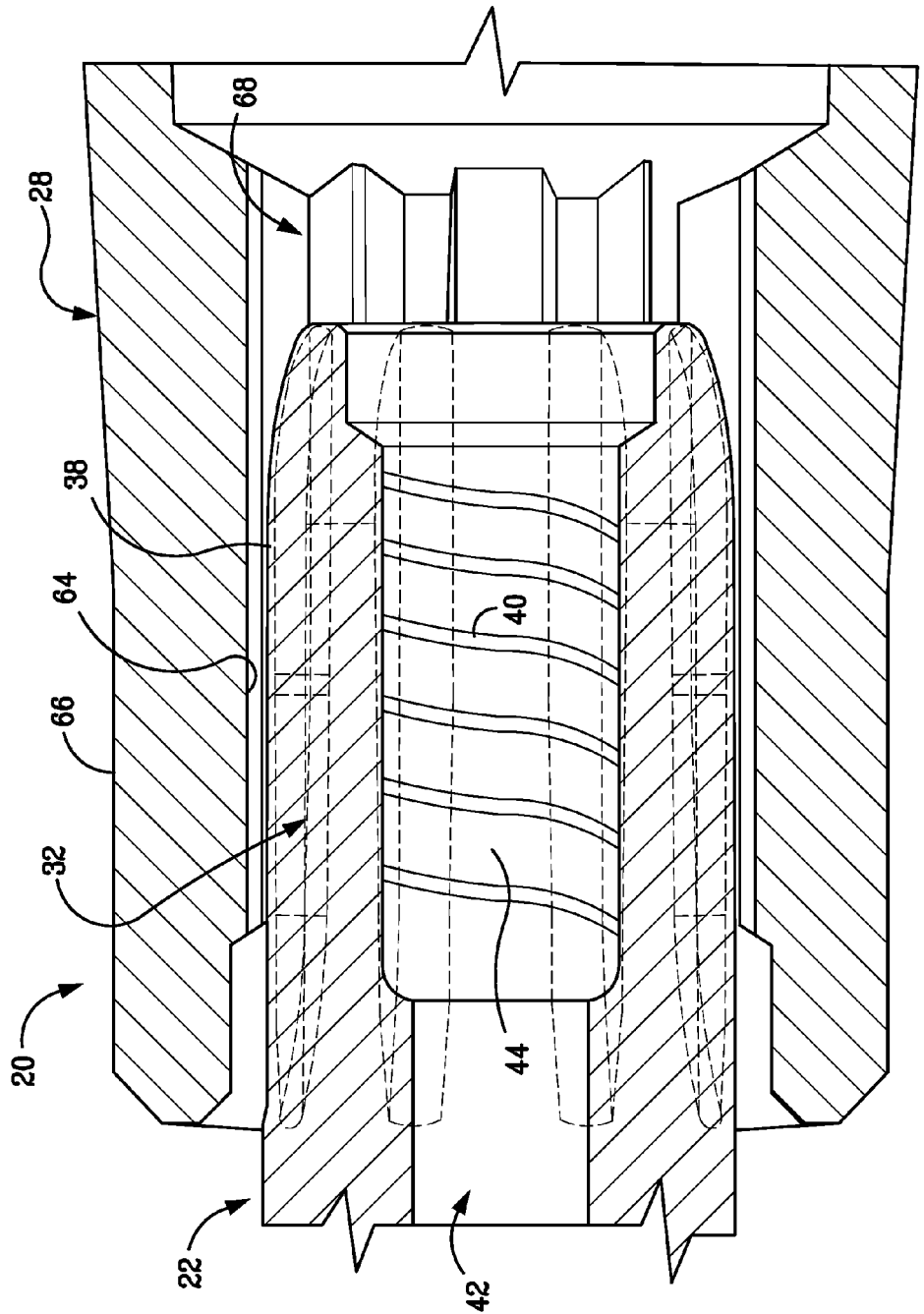
FIG. 4C is a sectional side elevation view of the bone anchor assembly illustrated in FIG. 4B, taken along line 4C-4C.
Figure 4D:
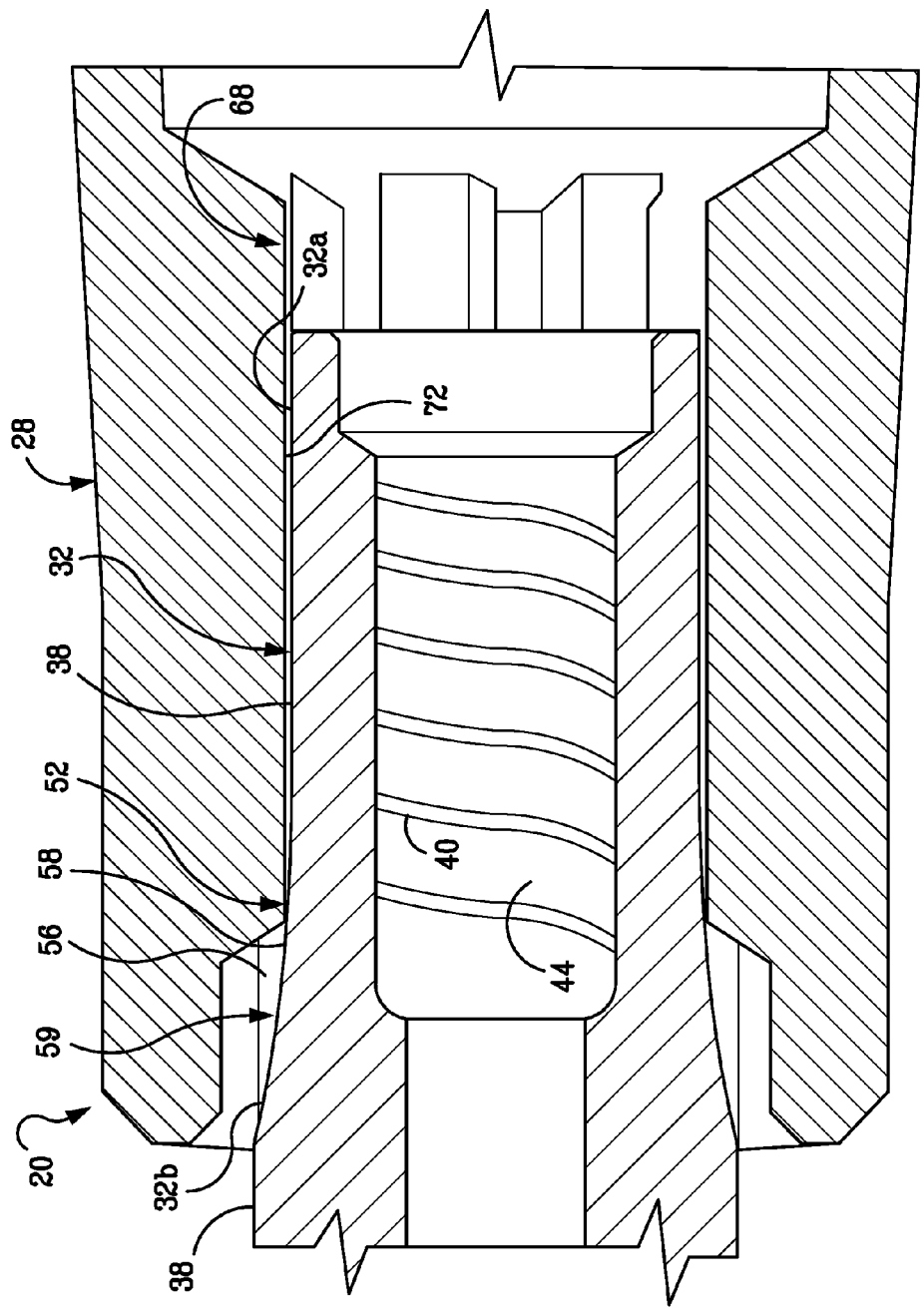
FIG. 4D is a sectional side elevation view of the bone anchor assembly illustrated in FIG. 4B, taken along line 4D-4D.

Referring now to FIGS. 3-4D, the driver instrument 28 includes a driver body 60 that defines a proximal attachment end 60a configured to be attach to any suitable handle, and a distal engagement end 60b configured to engage the bone anchor 22. The distal end 60b defines a longitudinally outward-facing end surface 61. The driver body 60 can be generally annular about a central longitudinal axis L2. While the body 60 is generally tapered radially inwardly along a direction from the distal end 60b toward the proximal end 60a, the body 60 can assume any desired size and geometric configuration suitable to drive the bone anchor 22. The driver body 60 defines a cannulation 62 extending longitudinally into the outer surface 61 at the distal end 60b. The cannulation 62 can define a shape corresponding to the shape of the outer surface 38 of the head 32. Accordingly, the cannulation 62 can be cylindrical, polygonal, or can define any alternative suitable shape as desired.

The driver body 60 defines a radially inner surface 64 that defines the interior cannulation 62, and an opposing radially outer surface 66. The driver body 60 includes a plurality of protrusions illustrated in accordance with one embodiment as teeth 68 that project radially in from the inner surface 64. Each tooth 68 generally corresponds in shape to the recesses 52. For instance, each tooth 68 includes a pair of opposing side walls 70, and a radially inner base 72 extending and connected between the radially inner ends of each side wall 70. The teeth 68 are longitudinally elongate, and thus parallel with the longitudinal axis L2. The teeth 68 are circumferentially spaced about the driver body 60, and thus define a spline drive engagement mechanism 65 configured to engage the spline drive mechanism 50 of the head 32 of the bone anchor 22. In accordance with one embodiment, eight teeth 68 are circumferentially spaced equidistantly about the outer surface 66 of the driver body 60, though it should be appreciated that the driver instrument 28 can alternatively include any number of teeth 68 as desired, such as four, six, ten, twelve or more recesses 68.

The side walls 70 can extend radially, or in a direction that includes a radial directional component. The side walls 70 of each recess 52 can extend along intersecting directions. For instance, the side walls 70 can converge toward each other with respect to a radially inward direction, or can diverge away from each other with respect to a radially inward direction. Alternatively still, the side walls 70 can extend parallel to each other. Additionally, portions of the side walls 70 of each tooth 68 can be parallel, while other portions can converge or diverge. In accordance with the illustrated embodiment, the side walls 70 converge toward each other with respect to a radially inward direction so as to provide an increased torque-receiving surface area, thereby increasing the torsional strength of each tooth 68.

The base 72 can extend circumferentially, or in a direction that includes a circumferential directional component. For instance, the base 72 can extend in a plane that is tangential to the circumferential direction. The base 72 of each tooth 68 can be perpendicular to one or both of the side walls 70, or can define an acute or obtuse angle with respect to one or both of the side walls 70. The side walls 70 may be blended into the base 72 with radii, angled/chamfered corners, or filleted corners. The driver instrument 28 thus defines a first cross-sectional distance or diameter D3 defined by the inner surface 64 the base 72 of opposing teeth 68 that is less than the first distance or diameter D1 (see FIGS. 4C-D), and a second cross-sectional distance or diameter D4 defined by the inner surface 64 at opposing locations between adjacent teeth 68. The first distance D3 is greater than the second distance D2 at the proximal end of the recesses 52, such that the base 72 of each tooth 68 is sized and configured to fit over and slide along the corresponding base 58 of a complementary recess 52 at the proximal end of the recess. The second distance D4 of the driver instrument 28 is greater than the first distance D1 of the head 32.

With continuing reference to FIGS. 4A-D, in operation, the proximal end 60a is grasped either manually or via an auxiliary handle, such that the cannulation 62 of the driver instrument 28 is generally longitudinally aligned with the outer surface 38 of the head 32, and the teeth 68 are generally aligned with the recesses 52. The driver instrument 28 attaches to the bone anchor 22 by translating one or both of the driver instrument 28 and the bone anchor toward each other along the longitudinal direction such that the cannulation 62 receives the proximal end 32a of the head 32. In particular, each of the teeth 68 is aligned with a select one of the recesses 52. Accordingly, as the driver instrument 28 and the bone anchor 22 are attached, the teeth 28 slide into the recesses 52 toward the longitudinally distal such that the base 72 of each tooth 68 faces the base 58 of the corresponding recess 52, and the side walls 70 of each tooth 68 face the side walls 56 of each corresponding recess 52. If pockets 39 are formed in the lip 35 as illustrated in FIG. 2A, the pockets can assist in removing an inserted threaded anchor that is surrounded by another implant (for instance a bone anchor connector) or bone.

Thus, once the distal end of the shaft 30 is placed against an underlying bone, the driver instrument 28 can rotated in a clockwise direction, thereby causing one of the side walls 70 to impart a torque/force against a corresponding one of the side walls 56 that causes the bone anchor 22 to correspondingly rotate in a clockwise direction, thereby advancing the bone anchor 22 into underlying bone. The driver instrument 28 can be subsequently rotated in a counterclockwise direction, thereby causing the other one of the side walls 70 to impart a torque/force against the corresponding side wall 56 that causes the bone anchor 22 to correspondingly rotate in a counterclockwise direction, thereby removing the bone anchor 22 from the underlying bone.

In accordance with one embodiment the tapered region 59 disposed at the distal end of at least one, up to all, of the recesses 52 causes the or distance or diameter D2 to gradually increase toward the proximal end of the recess 52. In accordance with one embodiment, the tapered region 59 tapers radially outward at an angle between approximately 0.25 degrees and approximately 5 degrees with respect to the longitudinal axis L1. The distance or diameter D2 of the recess 52 at the tapered region 59 increases to a distance greater than the second diameter D4 of the bases 72 of the teeth 68, thereby causing the teeth 68 to interfere with, or bite into, the corresponding base 58 of the recess 52 that receives the tooth 68 once the driver instrument 28 as the teeth 68 are translated into the distal ends of the recesses 52, so that the tooth 68 becomes wedged in the spline drive mechanism 50. The interference between the base 72 of the teeth 68 and the base 58 of the corresponding recesses 52 generally prevents the bone anchor 22 retained in the driver 28 from loosening or articulating during insertion or removal of the bone anchor 22.

As an additional strength benefit, the gradually increasing core diameter of the distal portion of the recesses 52 gradually improves the bending strength of the bone anchor 22 as the base diameter increases distally. In accordance with one embodiment, the bases 58 of the recesses 52 are blended with a radius into the converging angled side walls to further improve torsional strength and enhance the manufacturability of the recesses 52.

Alternatively or additionally, the distal end of the radially outer surface 38 can flare radially outward at a location between adjacent recesses 52, such that the inner surface 64 can interfere with the outer surface 38 at a location circumferentially between adjacent teeth 68. Alternatively or additionally, one or both the side walls 56 of at least one, up to all, of the recesses 52 can flare radially inward into the recess 52 at the distal end of the recess, such that the distal end of the recess defines a circumferential distance between the side walls 70 of the corresponding tooth 68 or teeth 68. Accordingly, as the teeth 68 are inserted into the distal end of the recesses 62, the teeth become pinched within the recesses 62, and interfere or bite into the side walls 56 of the recesses 52. Alternatively or additionally still, the proximal ends of at least one, up to all, the teeth 68 can flare radially outward thereby causing the proximal ends of the bases 72 to interfere with and bite into the base 58 of the corresponding recess 52 once the driver instrument 28 has engaged the head 32.

Accordingly, at least one of the teeth 68 and at least one of the recess 52 defines a surface that tapers in a direction toward the other of the tooth 68 and the recess 52, thereby causing at least one of the teeth 68 to frictionally interfere with the head 32 within the recess 52 that resists inadvertent removal of the driver instrument 28 from the head 32. In one embodiment, the tapered surface is a radially outwardly tapered region of the base 58 of the recess 52. Once the anchor 22 has been attached to underlying bone, a laterally outward force can overcome the frictional engagement caused by the tapered region so as to facilitate removal of the driver instrument 28 from the anchor 22.

As illustrated in FIG. 5C, the auxiliary device, such as the locator 46, can be threadedly connected to the head 32 in the bore 40 of the head 32 prior to attaching the driver instrument 28 to the head 32. Thus, the locator 46 has a length sized to fit within the cannulation 62 when the driver instrument 28 is fully attached to the head 32.

Referring again to FIG. 1A, once the bone anchors 22 are implemented as spine anchors and attached to an underlying pedicle, the clamp connector 26 is then applied over the head 32 at any desired position, including over the recesses 52 or a portion thereof, and the spinal rod 29 is connected between the clamp and a separate pedicle screw assembly, lamina hook, or other clamp assembly anchored to a separate vertebra to form a pedicle screw and rod construct for spinal correction.

Figure 6A:
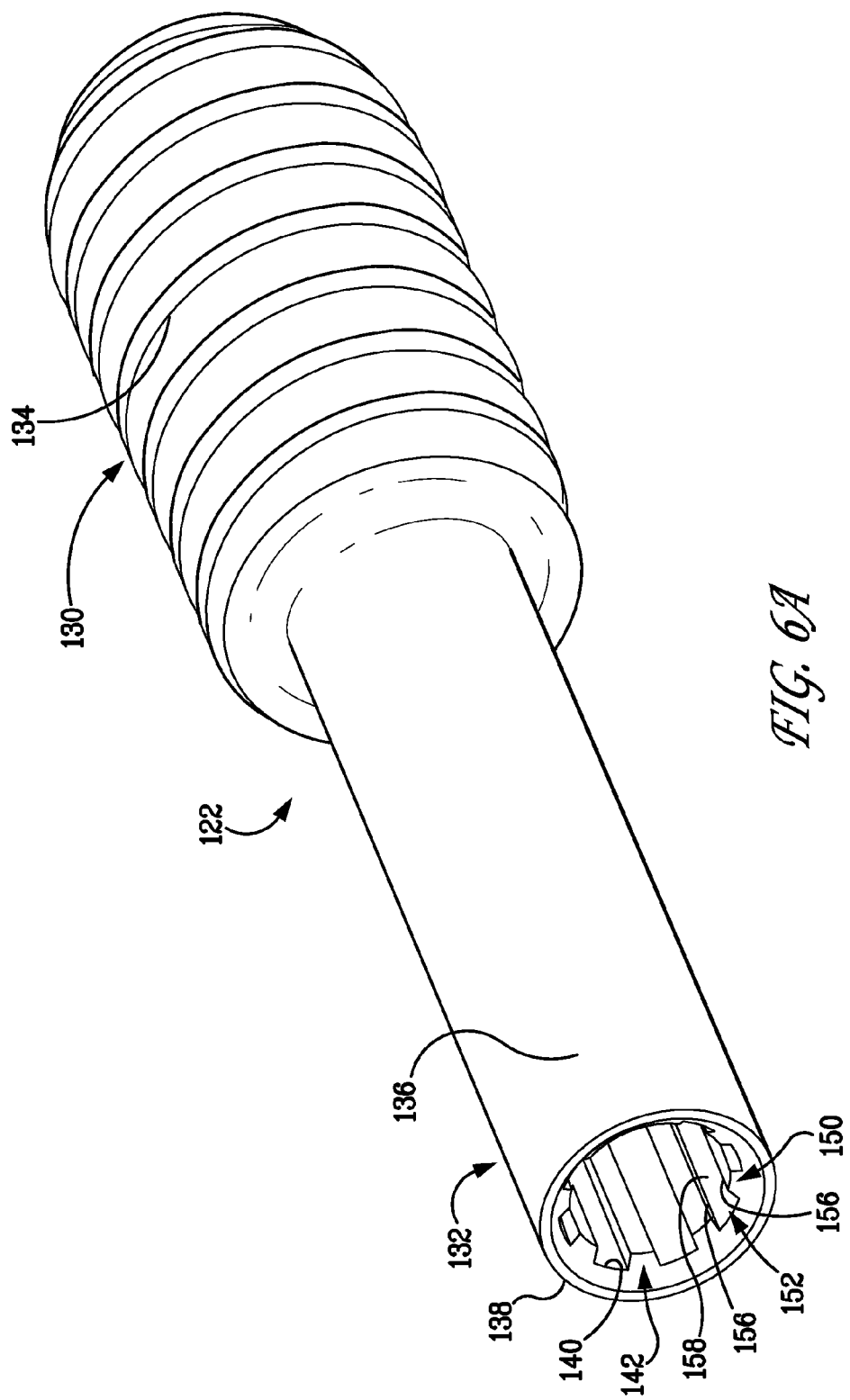
FIG. 6A is a perspective view of a bone anchor constructed in accordance with an alternative embodiment.
Figure 6B:
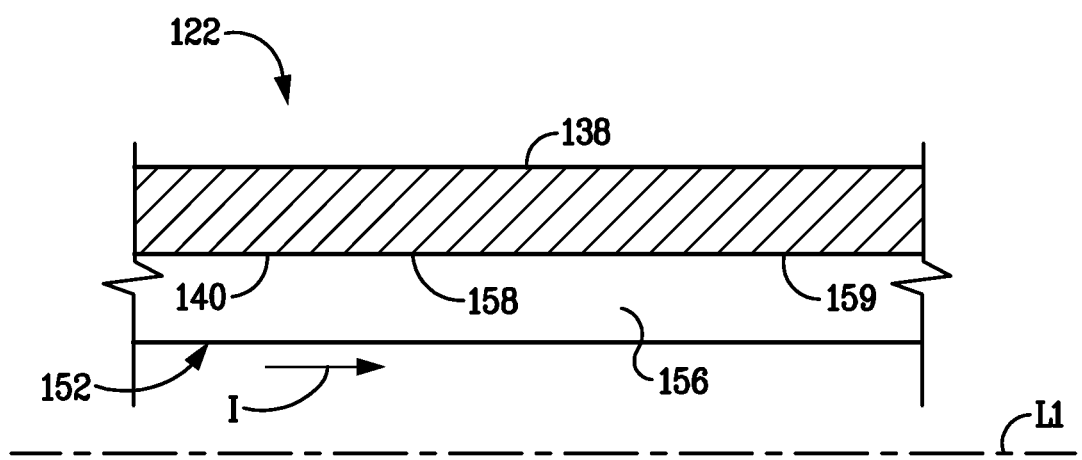
FIG. 6B is a sectional side elevation view of a portion of the bone anchor illustrated in FIG. 6A, showing a recess.

Referring now to FIGS. 6A-B, a bone anchor 122 can be provided in accordance with an alternative embodiment. The bone anchor 122 is illustrated having reference numerals corresponding to like structure of the bone anchor 22 incremented by 100 for the purposes of form and clarity. Thus, the bone anchor 122 includes a head 132 having a spline drive mechanism 150 formed in the inner surface 140 that is configured to attach to a complementary engagement member of the driver instrument. Thus, the spline drive mechanism 150 can be referred to as an internal spline drive mechanism. In particular, the head 132 includes an internal spline drive mechanism 150 disposed in the bore 142 that defines a plurality of recesses 152 projecting into the radially inner surface 140 in a radially outward direction. The radially outer surface 138 can define a diameter or other cross-sectional dimension that is greater than, substantially equal to, or less than that of the threads 134. The recesses 152 are longitudinally elongate, and circumferentially spaced about the head 32. In accordance with one embodiment, eight recesses 152 are circumferentially spaced equidistantly about the inner surface 140 of the head 32, though it should be appreciated that the head 132 can alternatively include any number of recesses 152 as desired, such as four, six, ten, twelve or more recesses 152.

Each recess 152 defines a pair of opposing radially extending side walls 156 and a base 158 disposed and connected between the radially inner ends of the side walls 156. It should be appreciated that the side walls 156 can extend radially, or in a direction that includes a radial directional component. The side walls 156 of each recess 152 can extend along intersecting directions. For instance, the side walls 156 can converge toward each other with respect to a radially outward direction, or can diverge away from each other with respect to a radially outward direction. Alternatively still, the side walls 156 can extend parallel to each other. Additionally, portions of the side walls 156 of each recess 152 can be parallel, while other portions can converge or diverge.

The base 158 can extend circumferentially, or in a direction that includes a circumferential directional component. For instance, the base 158 can extend in a plane that is tangential to the circumferential direction. The base 158 of each recess 152 can be perpendicular to one or both of the side walls 156, or can define an acute or obtuse angle with respect to one or both of the side walls 156. Within any or all of the recesses 152, the side walls 156 may be blended into the base 158 with radii, angled/chamfered corners, or filleted corners. At least one, up to all, of the recess 152 can include an inwardly tapered region 159 that flares radially inwardly with respect to the longitudinal axis L1 so as to engage a driver in the manner described above. For instance, the base 158 can be tapered radially inward at the distal end of one or more, up to all, of the recesses 152, such that the driver can be wedged between tapered regions of one or more opposing recesses 152 when the driver is inserted into the bore 142 along the direction of Arrow I. Alternatively or additionally, the side walls 156 of one or more, up to all, recesses 152 can be tapered toward each other at their distal ends.

The operation of the bone anchor 120 is similar to the operation of the bone anchor 20 shown in FIG. 1, with the exception that the driver instrument 28 is modified to operatively interlock inside the recesses 152. Accordingly, the protrusions or teeth 68 would project radially outward so as to fit in one or more, up to all, of the recesses 152 such that rotation of the driver instrument 28 correspondingly imparts torque/force to the bone anchor 122 in the manner described above. It should be appreciated that a distal region or end of the base 158 of at least a select one or more, up to all, of the recesses 152 tapers inwardly towards a corresponding one of the protrusions or teeth 68 that is disposed in the select one or more, up to all, of the recesses 152, such that the tapered region defines a cross-sectional distance of the head 28 that is less than a cross-sectional distance defined by bases 72 of opposing protrusions of the driver instrument 28.

The bone anchors 22 and 122, while illustrated as pedicle screws in accordance with one embodiment, can be constructed in accordance with any desired bone fixation application. For instance, the anchors 22 and 122 can provide polyaxial or monoaxial top-loading or side-loading pedicle screw assemblies with or without separate heads for attachment to spinal rods, bone screws used to anchor bone plates, wires, or other connectors for the stabilization of long bone fractures, cranial/maxillofacial fractures, or pelvic/sternal fractures, locking screws to attach "closed head" spinal hooks and screws to give the user an attachment point to manipulate the bone screw/hook amidst the bony anatomy, and before inserting a rod or tightening a locking screw, and any other bone anchor that is rotated to attach the bone anchor into underlying bone unless otherwise indicated.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

What is claimed:

1. A bone anchor comprising:
    a shaft that defines a distal end and a proximal end, the shaft extending along a longitudinal direction from the distal end to the proximal end, the shaft includes external threads that extend radially outward from the shaft at a location between the distal end and the proximal end such that the external threads define a first outer diameter; and
    a head connected to the proximal end of the shaft, the head including a body that defines an outer surface and a second outer diameter measured between opposed locations of the outer surface in a direction substantially perpendicular to the longitudinal direction, the head further including a spline drive mechanism that has a plurality of equidistantly spaced, longitudinally elongate recesses that extend into the body along a direction substantially perpendicular to the longitudinal direction such that each recess defines a pair of spaced side walls and a base extending between the pair of spaced side walls, such that the base and the side walls define a region configured to engage a mating driver instrument, at least one of the plurality of recesses defining a height measured from the base of the respective recess to a location of the body that is spaced from the base along a radial direction that is perpendicular to the longitudinal direction, and the height of the at least one of the plurality of recesses is different at a first location of the respective recess than a second location of the respective recess that is spaced from the first location along the longitudinal direction;

wherein the first outer diameter is greater than the second outer diameter.

2. The bone anchor as recited in claim 1, wherein each side wall is blended into the base.

3. The bone anchor as recited in claim 1, wherein the base of each recess is connected between radially outer ends of the side walls.

4. The bone anchor as recited in claim 1, wherein the base of each recess is connected between radially inner ends of the side walls.

5. The bone anchor as recited in claim 1, wherein the region is tapered.

6. The bone anchor as recited in claim 5, further comprising a central axis extending in the longitudinal direction, wherein the outer surface is the surface, the height of the at least one recess is measured from the base radially outward away from the central axis to the outer surface, such that the height decreases in the tapered region as the at least one recess extends longitudinally toward the distal end.

7. The bone anchor as recited in claim 5, further comprising a central axis extending in the longitudinal direction, wherein the body includes an inner surface opposite the outer surface, the inner surface defining an inner bore, and the inner surface is the surface, the height of the at least one recess is measured from the base radially inward toward the central axis to the inner surface, such that the height decreases in the tapered region as the at least one recess extends longitudinally toward the distal end.

8. The bone anchor as recited in claim 5, wherein the head defines a third outer diameter measured from the base of one recess to the base of an opposite recess in a direction substantially perpendicular to the longitudinal direction, and the third diameter is larger at a distal end of the recesses than at the proximal end of the recesses to create a tapered interference fit with the mating driver instrument.

9. The bone anchor as recited in claim 1, wherein the sidewall surfaces are each oriented at a non-perpendicular angle with respect to the base.

10. The bone anchor as recited in claim 1, wherein the head defines an inner surface that is opposite the outer surface, and the recesses project into the body from the outer surface in a direction substantially perpendicular to the longitudinal direction.

11. The bone anchor as recited in claim 1, wherein the head defines an inner surface that is opposite the outer surface, and the recesses project into the body from the inner surface in a direction substantially perpendicular to the longitudinal direction.

12. The bone anchor as recited in claim 1, wherein the head defines a threaded bore extending longitudinally therein.

13. The bone anchor as recited in claim 1, wherein the bone anchor is coated with a bone-growth stimulating surface.

14. The bone anchor as recited in claim 1, wherein the second outer diameter is measured between opposite outer surfaces each located between adjacent recesses.

15. The bone anchor as recited in claim 14, wherein the second outer diameter is between approximately 3 mm and approximately 5 mm.

16. The bone anchor assembly as recited in claim 14, wherein the second outer diameter is between approximately 4 mm and approximately 6 mm.

17. The bone anchor as recited in claim 1, wherein the head is configured to be coupled to a clamp that in turn is configured to connect the bone anchor to a fixation member.

18. The bone anchor as recited in claim 1, wherein the plurality of recesses are circumferentially spaced apart from each other.

19. The bone anchor as recited in claim 1, wherein the first outer diameter is constant at various locations along the longitudinal direction.

20. The bone anchor as recited in claim 1, wherein the first outer diameter increases at various locations along the longitudinal direction from the distal end towards the proximal end.

21. The bone anchor as recited in claim 1, wherein the shaft extends from the head along a distal direction, and the second location is spaced from the first location in the distal direction.

22. A bone anchor assembly comprising:
a bone anchor including:
a shaft that includes a distal end and a proximal end, the shaft extending from the distal end to the proximal end along a longitudinal direction, the shaft further including a threaded portion and an unthreaded portion, the threaded portion including external threads that extend radially outward from the shaft at a location between the distal end and the proximal end such that the external threads define a first outer diameter; and
a head connected to the shaft, the head including a body that defines an outer surface, the head defining a spline drive mechanism including a plurality of equidistantly spaced, longitudinally elongate recesses extending into the body such that each recess defines a pair of spaced side walls;
wherein neither the unthreaded portion of the shaft nor the outer surface of the head defines a diameter or other cross-sectional dimension that is greater than the first outer diameter and
a driver instrument including a plurality of protrusions configured to extend into at least one of the recesses, each protrusion including a pair of side walls, wherein one of the side walls is configured to engage a complementary side wall of one of the recesses so as to impart a torque/force onto the bone anchor head.

23. The bone anchor assembly as recited in claim 22, wherein the side walls of each recess each defines opposing ends, each recess comprises a base connected to the side walls at one of the opposing ends, and each protrusion comprises a base connected between the side walls of the protrusion.

24. The bone anchor assembly as recited in claim 23, wherein when the driver is engaged with the bone anchor, at least one of the recesses and the protrusions comprises a surface that tapers toward the other of the recesses and the protrusions so as to facilitate engagement of the recesses and the protrusions.

25. The bone anchor assembly as recited in claim 24, wherein the base of at least a select one of the recesses tapers outwardly towards a corresponding one of the protrusions that is disposed in the select one of the recesses, such that the tapered region defines a cross-sectional distance of the head that is greater than a cross-sectional distance defined by bases of opposing protrusions of the driver instrument.

26. The bone anchor assembly as recited in claim 24, wherein the base of at least a select one of the recesses tapers inwardly towards a corresponding one of the protrusions that is disposed in the select one of the recesses, such that the tapered region defines a cross-sectional distance of the head that is less than a cross-sectional distance defined by bases of opposing protrusions of the driver instrument.

27. The bone anchor assembly as recited in claim 22, wherein the head defines an outer surface and an opposing inner surface, and the recesses project into the outer surface of the head.

28. The bone anchor assembly as recited in claim 22, wherein the driver instrument defines a cannulation that fits over the outer surface of the head, and the protrusion extends into the cannulation.

29. The bone anchor assembly as recited in claim 22, wherein the head defines a threaded bore extending longitudinally therein, the bone anchor assembly further comprising an auxiliary device configured to be threadedly connected in the threaded bore.

30. The bone anchor assembly as recited in claim 22, wherein the head defines an outer surface and an opposing inner surface, and the recesses project into the inner surface of the head.

31. The bone anchor assembly of claim 22, wherein the plurality of recesses are circumferentially spaced apart from each other.

32. The bone anchor as recited in claim 22, wherein the first outer diameter is constant at various locations along the longitudinal direction.

33. The bone anchor as recited in claim 22, wherein the first outer diameter increases at various locations along the longitudinal direction from the distal end towards the proximal end.

34. A bone anchor comprising:
a shaft that defines a distal end and a proximal end, the shaft extending along a longitudinal direction from the distal end to the proximal end, the shaft includes external threads that extend radially outward from the shaft at a location between the distal end and the proximal end such that the external threads define a first outer diameter; and
a head connected to the proximal end of the shaft, the head including a body that defines an outer surface and a second outer diameter measured between opposed locations of the outer surface in a direction substantially perpendicular to the longitudinal direction, the head further including a spline drive mechanism that has a plurality of equidistantly spaced, longitudinally elongate recesses that extend into the body along a direction substantially perpendicular to the longitudinal direction such that each recess defines a pair of spaced side walls, the head further defining a threaded bore that extends in the longitudinal direction;
wherein the first outer diameter is greater than the second outer diameter.

35. The bone anchor of claim 34, wherein each of the recess defines a base extending between the pair of spaced side walls, such that the base and the side walls define a region configured to engage a mating driver instrument.

36. The bone anchor of claim 35, wherein at least one of the plurality of recesses defines a height measured from the base of the respective recess to a location of the body that is spaced from the base along a radial direction that is perpendicular to the longitudinal direction, and the height of the at least one of the plurality of recesses is different at a first location of the respective recess than a second location of the respective recess that is spaced from the first location along the longitudinal direction.

37. The bone anchor as recited in claim 36, wherein the shaft extends from the head along a distal direction, and the second location is spaced from the first location in the distal direction.

* * * * *